United States Patent [19]

Weber

[11] Patent Number: 5,393,798
[45] Date of Patent: Feb. 28, 1995

US005393798A

[54] HYDROGEL MATERIAL AND METHOD OF PREPARATION

[75] Inventor: Fredric J. Weber, Waco, Tex.

[73] Assignee: Spenco Medical Corporation, Waco, Tex.

[21] Appl. No.: 893,998

[22] Filed: Jun. 5, 1992

[51] Int. Cl.$^6$ .................. C08F 36/00; C08F 122/06; A61K 31/765
[52] U.S. Cl. .................. 521/149; 424/78.02; 424/78.06; 424/78.08; 424/78.33; 526/271
[58] Field of Search .................. 521/149; 424/78.02, 424/78.06, 78.08, 78.33; 526/271

[56] References Cited

U.S. PATENT DOCUMENTS

| | | | |
|---|---|---|---|
| 3,556,792 | 1/1971 | Katz | 96/35.1 |
| 3,556,793 | 1/1971 | Field et al. | 96/35.1 |
| 3,767,398 | 10/1973 | Morgan | 522/121 |
| 3,905,820 | 9/1975 | Frass | 522/121 |
| 4,226,232 | 10/1980 | Spence | 128/156 |
| 4,387,186 | 6/1983 | Williams et al. | 525/327.8 |
| 4,443,576 | 4/1984 | Bhattacharyya | 524/522 |
| 4,552,138 | 11/1985 | Hofeditz et al. | 128/156 |
| 4,631,227 | 12/1986 | Nakamura | 428/283 |
| 4,909,244 | 3/1990 | Quarfoot et al. | 128/156 |
| 4,930,500 | 6/1990 | Morgan | 128/156 |
| 5,050,424 | 10/1991 | Cartmell et al. | 424/443 |

FOREIGN PATENT DOCUMENTS

| | | | |
|---|---|---|---|
| 0097846 | 1/1984 | European Pat. Off. | 61/15 |
| 2009112 | 1/1970 | France | 8/15 |
| 1494113 | 7/1969 | Germany | 8/29 |
| 2416117 | 10/1975 | Germany | 8/32 |
| 62-121748 | 6/1987 | Japan . | |
| 62-297144 | 12/1987 | Japan . | |
| 0837926 | 6/1960 | United Kingdom . | |
| 837926 | 6/1960 | United Kingdom . | |
| 1085968 | 10/1967 | United Kingdom . | |
| 1342511 | 1/1974 | United Kingdom | C08F 27/08 |
| 1342511 | 1/1974 | United Kingdom . | |
| WO909883 | 7/1991 | WIPO | 8/12 |

Primary Examiner—Thurman K. Page
Assistant Examiner—Amy Hulina
Attorney, Agent, or Firm—Richards, Medlock & Andrews

[57] ABSTRACT

Hydrogel materials suitable for use in bandages and the like have been made from modified copolymers of poly(methyl vinyl ether/maleic anhydride). The modifying groups are three to seven carbon amines, amides or alcohols having a terminal vinyl group which may crosslink to other such modifiers or to intermediary difunctional coagents. A method for REDOX initiated crosslinking and continuous casting of the hydrogel, on a support material suitable for employment in a bandage, is also disclosed.

10 Claims, No Drawings

HYDROGEL MATERIAL AND METHOD OF PREPARATION

FIELD OF THE INVENTION

This invention relates to hydrogels which are crosslinked derivatives of poly(methyl vinyl ether/maleic anhydride) and their use in bandages, wound dressings and the like.

Background of the Invention

Various polymeric substances have been used, and proposed for use, as wound and burn treatments. These substances have variable properties, including the degree of hydration or water content. Further, the method of preparation influences the utility and economy of such substances for wound or burn care, because it is desirable to provide a material that is as free as possible from harmful residues, which may act as potential allergens or toxins, at a low cost. A hydrogel material may not be useful as a component in a bandage or wound dressing if it cannot maintain a physical shape for a relatively long period of time as opposed to flowing freely.

In U.S. Pat. No. 4,226,232 to Spence, a wound dressing is disclosed which contains a water-absorbent graft copolymer preferably comprised of hydrolyzed starch and polyacrylonitrile. This forms a gel when mixed with an appropriate amount of water and is useful as a component of a bandage or wound dressing. The '232 invention is an accepted wound treatment; but it is not ideally suited for long term usage, because it will flow when subjected to force or pressure. U.S. Pat. No. 4,552,138 to Hofeditz et al. discusses a wound dressing containing a hydrogel of polyvinyl alcohol crosslinked with formaldehyde. U.S. Pat. No. 4,631,227 is for a device used to apply water-soluble cosmetics to the skin. The water in the cosmetic preparation swells the dehydrated hydrogel prior to application.

U.S. Pat. No. 5,059,424 to Cartmell et al. considers a wound dressing hydrogel based on urethane chemistry composed of the adduct of an isophorone diisocyanate terminated prepolymer and a polyfunctional alcohol, wherein the hydrogel is cast into a thermoformed cavity. U.S. Pat. No. 4,930,500 is for a bandage that contains a hydrogel pad composed of crosslinked polyacrylamide extended with a polyol or glycol, while U.S. Pat. No. 4,909,244 to Quarfoot et al. covers a composite structure specifically adapted to absorb and hold large quantities of wound exudate as from a pressure sore or other skin ulcer.

None of the above patents disclose making the specific modified copolymers of the present invention which can be polymerized into hydrogels without radiation and which are suitable for a bandage production process.

Summary of the Invention

It has now been found that hydrogel materials with many desirable properties can be made by crosslinking modified copolymers of poly(methyl vinyl ether/maleic anhydride). The hydrogels have suitable characteristics for use as a wound dressing, since they exhibit a limited propensity to flow and can be formulated to have a water content in excess of 90%. Further, polymerization may be accomplished without radiation, or the necessity of intermediate coagents or bridging groups, thus limiting the risk of introducing undesirable residues in the wound dressing and having the further benefit of reducing cost of production. Further, the hydrogels are quite suitable for employment in an automated bandage production procedure.

The copolymers of the invention are made through modification of the anhydride moiety of water-insoluble poly(methyl vinyl ether/maleic anhydride) ("PVM/MAn") copolymers to form a copolymer having from about 15% to 100% of the maleic acid carboxyl groups grafted with an unsaturated amine or alcohol to form a monoamide or monoester of poly(methyl vinyl ether/maleic acid) "PVM/MA". These are referred to as graft copolymers, a copolymer molecule comprised of a main backbone chain to which side chains containing different atomic constituents are attached at various points. Preferably, the modifying amine has three to seven carbon atoms and is of the structure $NH_2—(CH_2)_{1-5}—CH=CH_2$ or

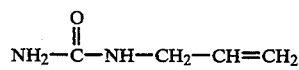

(allylurea). Most preferably, allylamine ($NH_2—CH_2—CH=CH_2$) is employed as the modifying amine.

A modifying alcohol is selected from those containing a pendent vinyl group and is of a length of three to seven carbon atoms: $HO—(CH_2)_{1-5}—CH=CH_2$. Most preferably, allyl alcohol ($HO—CH_2—CH=CH_2$) or 3-butene-1-ol ($HO—CH_2—CH_2—CH=CH_2$) are selected.

The modification of the PVM/MAn copolymer through grafting yields a material that is water soluble and may be converted into a hydrogel material through crosslinking of the grafted vinyl groups in the modified portion of adjacent copolymer molecules.

It has also been found that the grafted PVM/MA product of this invention can be effectively crosslinked via a method of careful independent metering and mixing of a solution consisting of (1) a water-soluble crosslinking agent and (2) a solution of the grafted copolymer(s) wherein the two solutions are combined and the crosslinking reaction initiates instantaneously. A crosslinking agent is selected that is not reactive with carboxylate groups in the PVM/MA copolymer per se, but is reactive with the pendent vinyl groups of the grafted compounds. A casting head can be used to immediately cast the combined solutions upon a suitable support material in order to make a sheet or strip of hydrogel laminated to a support material. These sheets or strips can subsequently be cut into the desired shapes for employment in bandages, dressings and the like.

DETAILED DESCRIPTION OF THE INVENTION

The hydrogel materials of this invention are modified copolymers of poly(methyl vinyl ether/maleic acid) ("PVM/MA"). The modified copolymers essentially have the following repeating structural subunits, although the number of anhydride groups that are reacted with a modifying ("R") group depends on the amount of modifier added and the time of reaction:

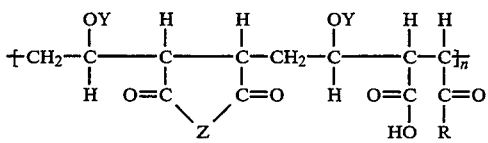

where n is an integer greater than one representing the number of structural units in a copolymer chain $$R = -NH-(CH_2)_{1-5}-CH=CH_2,$$

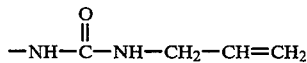

or $$-O-(CH_2)_{1-5}-CH=CH_2;$$

Y is an alkyl group having from one to three carbons, and Z is either a bivalent oxygen atom or one hydroxyl group and one R group. Thus, the portion of the unit containing Z may be an unreacted anhydride, where Z is one bivalent oxygen atom as follows:

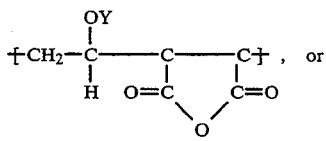

the portion of the unit containing Z will be identical to the other portion of the unit when Z is one hydroxyl and one R group:

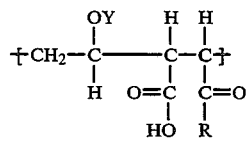

Preferably, an amine is used as a modifier to form an amide. Most preferably, allylamine or allylurea are used as modifiers. When an ester is formed rather than an amide, it is preferred that either allyl alcohol or 3-butene-1-ol be used.

The modified copolymers are preferably crosslinked via linkage of the pendent vinyl group of the modifying "R"group with another similar group on an adjacent molecule to form a three dimensional molecular network or "gel". During formation of the hydrogel, the use of an aqueous solvent may convert Z groups constituting a bivalent oxygen atom to two hydroxyl groups, i.e., a dicarboxylic acid.

Poly(methyl vinyl ether/maleic anhydride) is preferably used as a starting material ("PVM/MAn"). PVM/MAn can be made according to methods known in the art or purchased commercially. It is commercially available under the trade name Gantrez® AN from ISC Specialty Products Corp. Various molecular weights are commercially offered ranging from about 20,000 to 80,000. PVM/MAn appropriate for the invention may have a molecular weight of from about 20,000 to about 500,000. Of the commercially available PVM/MAn, it is most preferred to employ those having higher molecular weights.

The PVM/MAn is first dissolved in a suitable aprotic solvent. A suitable solvent solubilizes both the PVM/MAn and the modifying compounds. The solvent must also be readily removed during the isolation step such that any residual amount would come off in a volatilizing operation under reduced pressure and/or moderate heat, such as vacuum drying. Suitable solvents include, but are not limited to, dimethyl formamide (DMF) and/or tetrahydrofuran (THF).

Sufficient solvent is utilized to allow the copolymer chains to be fully extended in the solvent rather than coiled. This is to insure that subsequent modifications will not be retarded by conformational inaccessibility of reactive sites along the copolymer backbone. More solvent is generally required for higher molecular weight material, since solutions of it are usually of higher viscosity. Generally, an appropriate extent of dissolution will be achieved with a concentration of PVM/MAn in solvent of about 0.5 to 100 g per liter. For Gantrez® AN-149, which is specified to have a molecular weight of approximately 50,000, a suitable ratio has been found to be about 30-60 grams per liter. The characteristics of the solution of Gantrez® AN-149 can be used as a standard or guideline for determining the amount of solvent to employ with higher molecular weight copolymer.

To achieve complete solubilization, the solvent-PVM/MAn mixture is heated to about 50° C. to about 75° C., preferably about 55° C. Once solution is effected, the modifying reaction is initiated.

A half-amide form of the PVM/MA copolymer is prepared by adding an amine described above alone, or in similar solvent, to the dissolved PVM/MAn described above. An amount is added on a molar basis to effect the desired degree of substitution from about 15% to 100% of the maleic anhydride portions of the copolymer.

The reaction is exothermic and raises the temperature to about 65° C. to about 90° C. It is allowed to react for about 30 to about 45 minutes. The reaction mixture is then allowed to cool. The halfamide form of the graft copolymer can be recovered from the mixture by addition of a non-polar hydrocarbon solvent, such as cyclohexane or heptane, which will precipitate the half-amide. The half-amide can be recovered from the mixture, dried, and ground to a powder if desired.

Alternatively, half esters of the copolymer can be made using an unsaturated alcohol having the characteristics previously described. It is preferred that the alcohol be added to the copolymer solution as an alkoxide anion, which can be accomplished by making a solution of the alcohol with NaOH, KOH or similar inorganic base. The mixture is allowed to react as described for the amide. The half-ester is recovered as described for the half-amide structure.

The half-amide and half-ester structures are referred to as the modified copolymers. A crosslinked hydrogel is then prepared from the modified copolymers dissolved in an aqueous solvent. A crosslinking initiator system is selected which is water soluble and does not react with COOH groups but does react favorably with the terminal double bond in the modifying groups. It is also desirable that initiators be completely exhausted in the crosslinking process and leave no residues. The crosslinking initiator system can be any water-soluble initiator or initiator pair. The crosslinking initiating system, thus, has different portions: one oxidizing, one reducing. Preferable initiators include oxidation/reduction electron transferring pairs of compounds referred to as a REDOX couple. Typical water-soluble REDOX couples include persulfate/ferrous ion salts, persulfate/thiosulfate salts, persulfate/bisulfate salts, hydrogen peroxide ($H_2O_2$)/ferrous ion salts, and $H_2O_2$/L-ascorbic acid (vitamin C). The persulfate, bisulfate and thiosulfate counter ions can be $Na^+$, $K^+$ or $NH_4^+$. Other combinations are possible as long as they exhibit some measure of water solubility (0.1% or higher). Difunctional coagents, having terminal vinyl groups at opposite ends of their molecule may, be included as part of the crosslinking process, but this is not necessary.

Preferably, the reacting solutions of modified copolymer and crosslinking agent may be cast on a support material, such as polyester film (Mylar ®), and overlaid with a reinforcing scrim material that has a high porosity and is, therefore, permeable to fluids of relatively high viscosity. Typical reinforcing scrims include embossed nonwoven polyolefin fabrics commercially available as Delnet ® X-220, or X-230 from Applied Extrusion Technologies, Wilmington, Del, or random lay spunbonded polyester nonwovens, like Reemay ® series 2000 or 2200 materials, available from Reemay Inc., Old Hickory, Tenn. It is preferable to overlaminate the hydrogel with an appropriate protective liner suitable to prevent moisture evaporation, such as, for example, low density polyethylene film (LDPE).

In the alternative, the hydrogel can be dried, and a protective liner applied, if desired, to keep the hydrogel dust free and clean.

The hydrogel can be used in a bandage or wound dressing which can be manufactured according to any suitable method. A roll of the laminated support, scrim and hydrogel can be employed in various automated bandage manufacturing operations known in the art.

The following examples are intended to illustrate the invention.

EXAMPLE 1

Preparation of Modified Copolymer—Half-Amide

Thirty grams of Gantrez ® AN-149 copolymer was added to 450 ml of THF, and the mixture was heated to 55° C. to effect a solution. At that point, a solution of 4.4 g of allylamine in 50 ml of THF was added dropwise at essentially a constant rate to the copolymer solution over a period of 30 minutes. Over this period, the temperature of the copolymer solution increased from 55° C. to approximately 65° C. Agitation continued for a period of 15 minutes after complete addition of the allylamine solution. At this point, 400 ml of reagent hexanes was added to the solution which was allowed to reflux at around 66°–69° C. for a period of 15 minutes. A resinous precipitate formed which was filtered through glass fiber, washed with additional hexanes and dried in a vacuum desiccator. Yield was 26.4 grams of 40% (molar) substituted half-amide version of the modified copolymer.

EXAMPLE 2

Preparation of Modified Copolymer—Half-Ester

Thirty grams of Gantrez ® AN-179 copolymer was added to 400 ml of DMF, and the mixture was heated to 55° C. to effect solution. Next, a solution of 9.9 ml (0.115M) 3-butene-1-ol dissolved in 50 ml DMF and 11.5 ml of 10M NaOH was added dropwise at essentially a constant rate to the copolymer solution over a period of 20 minutes. The NaOH solution catalyzed the grafting of the 3-butene-1-ol by converting the alcohol to the alkoxide anion. The 11.5 ml of 10M NaOH is equimolar with the 3-butene-1-ol. A resinous precipitate began to form immediately upon addition of the 3-butene-1-ol/NaOH solution. This precipitate was recovered, as indicated above, to yield 22.1 g of 60% (molar) substituted half-ester version of the copolymer.

EXAMPLE 3

Crosslinking the Modified Copolymers

A 0.5M solution of hydrogen peroxide ($H_2O_2$) in deaerated water or other water-soluble crosslinking initiator may be prepared and placed in a first reservoir. A 6% to 10% mixture of the modified copolymer, containing 0.1% L-ascorbic acid, is made up in distilled water and placed in a second reservoir, agitated continuously, and deaerated.

Each reservoir feeds a separate chemical metering pump that, in turn, regulates the flow of each deaerated component to a common static mixer. A crosslinked hydrogel, made up to a 5% gel content, can be accomplished by metering of equivalent masses of a 10% mixture of the modified copolymer solution and the 0.5M solution of hydrogen peroxide into the static mixer where crosslinking begins upon contact of the two solutions.

The static mixer is connected to a casting head which casts 2" wide strips of the reactive fluid mixture onto a moving web of material, typically polyester (PET) film. Four parallel 2" wide strips of 5% crosslinked hydrogel, at a line speed of 2 meters/minute, can be produced by the metering of 268 grams of the 10% solution of grafted copolymer and 268 grams of the hydrogen peroxide solution.

I claim:

1. A hydrogel material comprising crosslinked copolymer chains of alkyl vinyl ether and maleic anhydride wherein said copolymer chains comprise the repeated structural unit:

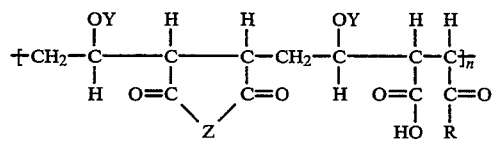

wherein n is an integer greater than one representing the number of said structural units in each of said copolymer chains, Y is an alkyl group having one to three carbon atoms, and wherein R is a modifying group selected from the group consisting of -NH—($CH_2$)$_{1-5}$—CH=$CH_2$ and

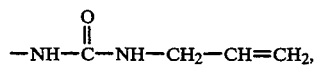

Z is selected from one bivalent oxygen atom, two hydroxyl groups or one hydroxyl group and one R group, and wherein one of said copolymer chains is crosslinked to another of said copolymer chains via linkage of an R group of one of said copolymer chains with an R group of another of said copolymer chains.

2. The hydrogel material of claim 1 wherein Y is —$CH_3$.

3. The hydrogel material of claims 1 or 2 wherein R is —NH—$CH_2$—CH=$CH_2$).

4. The hydrogel material of claims 1 or 2 wherein R is 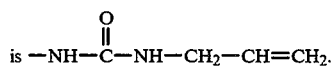

5. The hydrogel material of claim 1 wherein from about 15% to about 100% of the maleic anhydride portion of said copolymer are modified by reaction with said modifying group.

6. A hydrogel material comprising crosslinked copolymer chains of alkyl vinyl ether and maleic anhydride, each of said copolymer chains comprises the repeated structural unit:

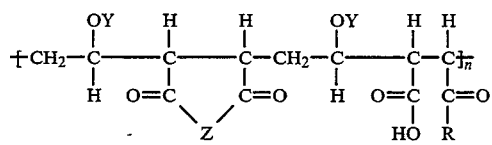

wherein n is an integer greater than one representing the number of said structural unit in each of said copolymer chains, Y is an alkyl group having one to three carbon atoms, Z is selected from one bivalent oxygen atom, two hydroxyl groups or one hydroxyl group and one R group, R is an unsaturated alcohol radical, and wherein one of said copolymer chains is crosslinked to another of said copolymer chains via linkage of an R group of one of said copolymer chains with an R group of another of said copolymer chains.

7. The hydrogel material of claim 6 wherein said unsaturated alcohol radical is $-O-(CH_2)_{1-5}-CH=CH_2$.

8. The hydrogel material of claim 7 wherein said unsaturated alcohol radical is allyl alcohol or 3-butene-1-ol.

9. The hydrogel material of claim 5, wherein about 40%–100% of the maleic acid portion of said copolymer is modified by reaction with said modifying group.

10. The hydrogel material of claim 6, wherein about 40%–100% of the maleic acid portion of said copolymer is modified by reaction with said modifying group.

* * * * *